US00PP33499P3

(12) United States Plant Patent
Post

(10) Patent No.: US PP33,499 P3
(45) Date of Patent: Sep. 21, 2021

(54) ***CHRYSANTHEMUM* PLANT NAMED 'DLFDLIC4'**

(50) Latin Name: ***Chrysanthemum* X *morifolium***
Varietal Denomination: DLFDLIC4

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 17/089,725

(22) Filed: Nov. 5, 2020

(65) Prior Publication Data

US 2021/0136979 P1 May 6, 2021

Related U.S. Application Data

(60) Provisional application No. 62/973,983, filed on Nov. 5, 2019.

(51) Int. Cl.
*A01H 5/02* (2018.01)
*A01H 6/14* (2018.01)

(52) U.S. Cl.
USPC ..... Plt./278
CPC ..... *A01H 6/1424* (2018.05)

(58) Field of Classification Search
USPC ..... Plt./278
CPC ..... A01H 6/1424
See application file for complete search history.

*Primary Examiner* — Anne Marie Grunberg
(74) *Attorney, Agent, or Firm* — C. Anne Whealy

(57) ABSTRACT

A new and distinct cultivar of *Chrysanthemum* plant named 'DLFDLIC4', characterized by its upright plant habit; vigorous growth habit and rapid growth rate; dark green-colored leaves; uniform and freely flowering habit; strong upright flowering stems with numerous inflorescences; single-type inflorescences with red-colored ray florets and bright yellow-colored disc florets; relative tolerance to low production temperatures; resistance to Fusarium Wilt and White Rust; and good postproduction longevity.

2 Drawing Sheets

Figure 1:
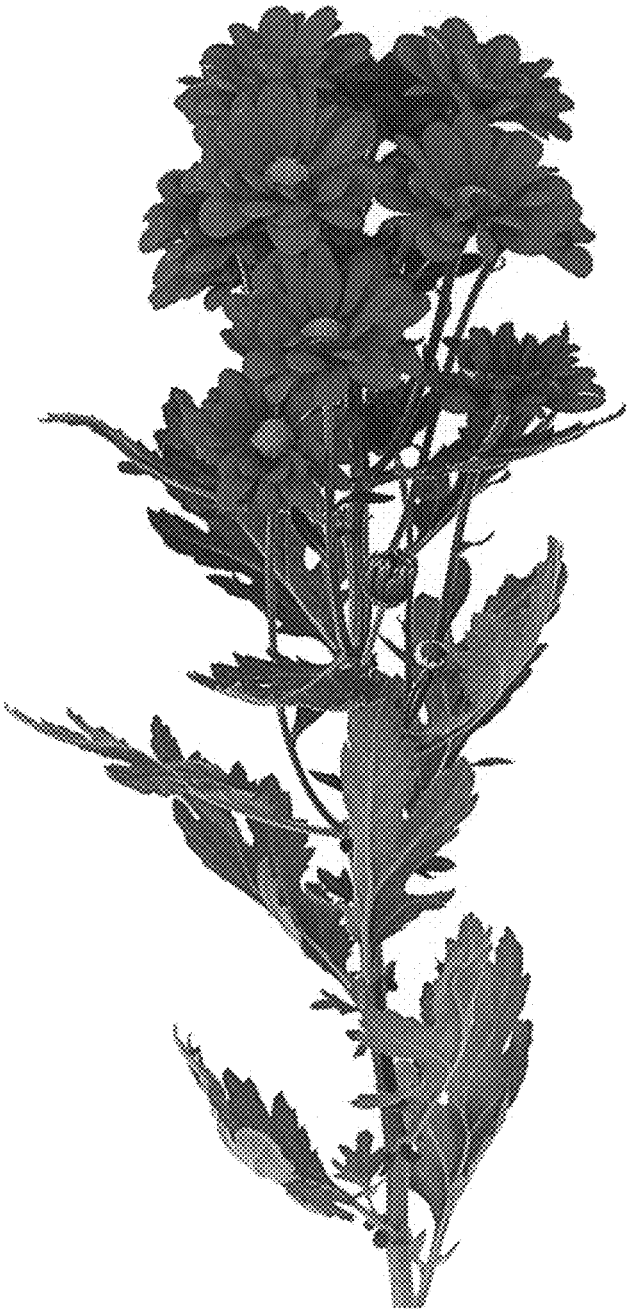
Figure 2:
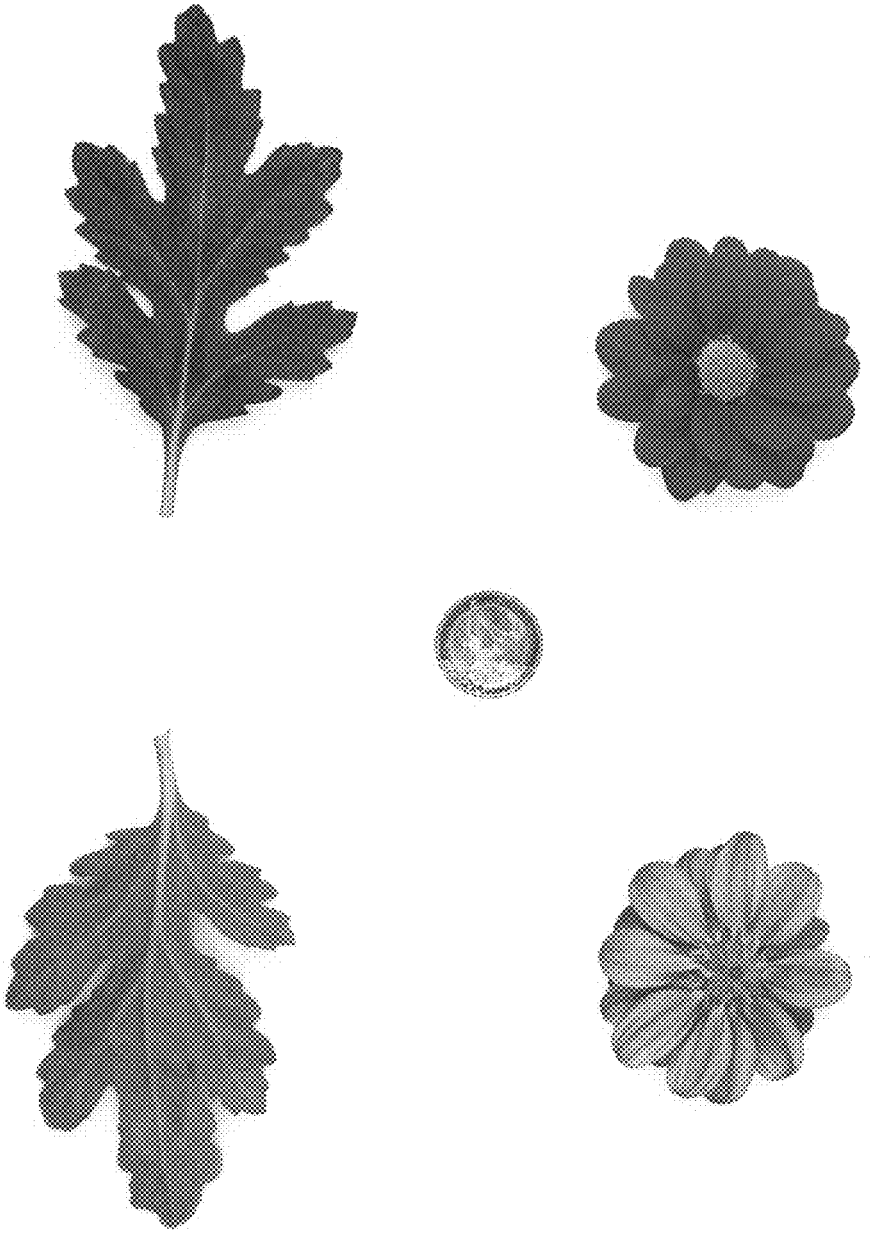

Botanical designation: *Chrysanthemum* X *morifolium*.
Cultivar denomination: 'DLFDLIC4'.

CROSS-REFERENCED TO CLOSELY-RELATED APPLICATIONS

Title: Varieties of *Chrysanthemum* Plants
Inventor/Applicant: Arie Gerard Post
Filed: Nov. 5, 2019
Ser. No.: 62/973,983
Inventor/Applicant hereby claim the benefit of this provisional U.S. Patent Application.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFDLIC4'.

The new *Chrysanthemum* plant is a product of a planned breeding program conducted by the Inventor in Maasdijk, The Netherlands. The objective of the breeding program is to create new cut flower *Chrysanthemum* plants with numerous attractive inflorescences.

The new *Chrysanthemum* plant originated from a cross-pollination in March, 2013 of a proprietary selection of *Chrysanthemum* x *morifolium* identified as code number db 31968, not patented, as the female, or seed, parent with a proprietary selection of *Chrysanthemum* x *morifolium* identified as code number db 11482, not patented, as the male, or pollen, parent. The new *Chrysanthemum* plant was discovered and selected as a single flowering plant from within the progeny of the stated cross-pollination in a controlled greenhouse environment in Maasdijk, The Netherlands in November, 2014.

Asexual reproduction of the new *Chrysanthemum* plant by vegetative terminal cuttings since November, 2014 in Maasdijk, The Netherlands has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFDLIC4'. These characteristics in combination distinguish 'DLFDLIC4' as a new and distinct *Chrysanthemum* plant:

1. Upright plant habit.
2. Vigorous growth habit and rapid growth rate.
3. Dark green-colored leaves.
4. Uniform and freely flowering habit.
5. Strong upright flowering stems with numerous inflorescences.
6. Single-type inflorescences with red-colored ray florets and bright yellow-colored disc florets.
7. Relatively tolerant to low production temperatures.
8. Resistant to Fusarium Wilt and White Rust.
9. Good postproduction longevity.

Plants of the new *Chrysanthemum* differ primarily from plants of the female parent selection in ray floret color as plants of the new *Chrysanthemum* have lighter red-colored ray florets than plants of the female parent selection. In addition, plants of the new *Chrysanthemum* are more low temperature tolerant than plants of the female parent selection.

Plants of the new *Chrysanthemum* differ primarily from plants of the male parent selection in ray floret color as plants of the new *Chrysanthemum* have red-colored ray florets whereas plants of the male parent selection have purplish red-colored ray florets. In addition, plants of the new *Chrysanthemum* are resistant to White Rust whereas plants of the male parent selection are susceptible to White Rust.

Plants of the new *Chrysanthemum* can be compared to plants of *Chrysanthemum* X *morifolium* 'DLFELLO', not patented. In side-by-side comparisons, plants of the new *Chrysanthemum* differ primarily from plants of 'DLFELLO' in ray floret color as plants of the new *Chrysanthemum* have red-colored ray florets whereas ray florets of 'DLFELLO' are deep red in color. In addition, plants of the new *Chrysanthemum* have larger inflorescences than plants of 'DLFELLO'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet comprises a side perspective view of a typical flowering stem of 'DLFDLIC4' grown as a spray-type cut flower.

The photograph on the second sheet is a close-up view of upper (top of the photographic sheet) and lower (bottom of the photographic sheet) surfaces of typical leaves (left) and inflorescences (right).

DETAILED BOTANICAL DESCRIPTION

The aforementioned photographs and following observations and measurements describe plants grown during the late spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were nine weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFDLIC4'.

Parentage:

*Female, or seed, parent.*—Proprietary selection of *Chrysanthemum* x *morifolium* identified as code number db 31968, not patented.

*Male, or pollen, parent.*—Proprietary selection of *Chrysanthemum* x *morifolium* identified as code number db 11482, not patented.

Propagation:

*Type.*—Terminal vegetative cuttings.

*Time to initiate roots, summer.*—About four days at temperatures about 20° C.

*Time to initiate roots, winter.*—About six days at temperatures about 20° C.

*Time to produce a rooted young plant, summer.*—About twelve days at temperatures about 20° C.

*Time to produce a rooted young plant, winter.*—About 14 days at temperatures about 20° C.

*Root description.*—Fine, fibrous; typically light brown in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous single-type cut flower that is typically grown as a single stem spray-type; upright plant habit; vigorous growth habit and rapid growth rate.

*Plant height, soil level to top of foliar plane.*—About 78 cm.

*Plant height, soil level to top of inflorescence plane.*—About 84.4 cm.

*Plant (spray) diameter.*—About 21 cm.

*Flowering stem length.*—About 74.5 cm.

*Flowering stem diameter.*—About 7 mm.

*Flowering stem internode length.*—About 2.8 cm.

*Flowering stem strength.*—Strong.

*Flowering stem aspect.*—Erect.

*Flowering stem texture and luster.*—Densely pubescent; slightly glossy.

*Flowering stem color, developing.*—Close to 144A.

*Flowering stem color, developed.*—Close to between 143A and 144A.

*Leaf description.*—Arrangement: Alternate; simple. Length: About 12 cm. Width: About 7.4 cm. Shape: Oblong to ovate and obovate. Apex: Abruptly acute. Base: Attenuate. Margin: Palmately lobed, coarsely serrate to dentate; sinuses convergent and medium to deep in depth. Texture and luster, upper surface: Moderately pubescent, not rugose; moderately velvety; slightly glossy. Texture and luster, lower surface: Moderately pubescent, prominent venation; slightly velvety; slightly glossy. Venation pattern: Pinnate, reticulate. Color: Developing leaves, upper surface: Close 137A. Developing leaves, lower surface: Close to 146B. Fully developed leaves, upper surface: Close to NN137A; venation, close to 147C. Fully developed leaves, lower surface: Close to 137B; venation, close to 146C. Petioles: Length: About 1.8 cm. Diameter: About 3 mm by 4 mm. Strength: Moderately strong. Texture and luster, upper and lower surfaces: Moderately to densely pubescent; slightly glossy. Color, upper surface: Close to 146C; edges, darker than 143A. Color, lower surface: Close to 146B to 146C; edges, close to between 137A and 143A. Stipules: Quantity and appearance: Two leafy stipules, opposite, at the petiole attachment to the stem. Length: About 7 mm. Width: About 1 cm. Shape: Reniform. Texture and luster, upper surface: Moderately pubescent, not rugose; moderately velvety; slightly glossy. Texture and luster, lower surface: Moderately pubescent, prominent venation; slightly velvety; slightly glossy. Color, upper surface: Close to NN137A. Color, lower surface: Close to 137B.

Inflorescence description:

*Appearance*.—Single-type inflorescence form with narrowly obovate-shaped ray florets and tubular disc florets; inflorescences borne perpendicular to peduncles and face mostly upright to slightly outwardly; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 48 days later when grown as a spray-type.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 20 inflorescences develop per flowering stem.

*Inflorescence size*.—Diameter: About 6.7 cm. Depth (height): About 2.6 cm. Disc diameter: About 1.6 cm.

*Receptacles*.—Height: About 5.5 mm. Diameter: About 7 mm. Shape: Globular. Color: Close to 145D; at the margins, close to 145B.

*Inflorescence buds*.—Height: About 1.5 cm. Diameter: About 1.3 cm. Shape: Broadly ovate. Texture and luster: Distally, smooth and glabrous; proximally, moderately pubescent; slightly to moderately glossy. Color: Close to 143B; immature ray florets, close to 183C to 183D.

*Ray florets*.—Quantity and arrangement: About 26 arranged in about two whorls. Length: About 3.3 cm. Width: About 1.4 cm. Shape: Obovate; slightly concave and moderately carinate. Apex: Obtuse to shallowly emarginate. Base: Broadly attenuate. Margin: Entire; not undulate. Aspect: Initially upright to about 62.5° from vertical. Texture and luster, upper surface: Smooth, glabrous; velvety; matte. Texture and luster, lower surface: Smooth, glabrous; slightly velvety; slightly glossy. Color: When opening, upper surface: Close to 53A. When opening, lower surface: Close to 174C and 178C. Fully opened, upper surface: Slightly darker than 179A; at the base, close to 2B; venation, similar to lamina colors; color does not change with development. Fully opened, lower surface: Close to 166D and N170B; at the base, close to 154B and 154C; venation, similar to lamina colors; color does not change with development.

*Disc florets*.—Quantity and arrangement: About 220 massed at the center of the receptacle. Length: About 6 mm. Diameter: About 1.25 mm. Shape: Lower 85% fused into a tube; upper 15% free. Apex: Narrowly acute. Margin, free-part: Entire. Texture and luster, inner and outer surfaces: Smooth, glabrous; glossy. Color, when opening, inner and outer surfaces: Distally, close to 6C; at the apex, close to 5A to 5B; and proximally, close to 145C. Color, fully opened, inner and outer surfaces: Distally, close to 6B to 6C; at the apex, close to 5A; and proximally, close to 145C.

*Involucral bracts*.—Quantity and arrangement: About 20 arranged in about two whorls. Length: About 7 mm. Width: About 3.5 mm. Shape: Ovate to narrowly ovate. Apex: Obtuse. Base: Cuneate. Margin: Entire. Texture and luster, upper surface: Smooth, glabrous; glossy. Texture and luster, lower surface: Moderately to densely pubescent; matte. Color, upper surface: Close to 141A; margins, translucent and close to 157C and N199A. Color, lower surface: Close to 138A; towards the apex, close to 147B; margins, translucent and close to 157C and N199A.

*Peduncles*.—Length, terminal peduncle: About 6.3 cm. Diameter, terminal peduncle: About 3 mm. Length, third peduncle: About 9 cm. Diameter, third peduncle: About 3 mm. Strength: Strong. Aspect, terminal peduncle: Mostly upright. Aspect, third peduncle: About 30° from the flowering stem axis. Texture and luster: Densely pubescent; very slightly glossy. Color: Close to 143A.

*Reproductive organs*.—Androecium: Present on disc florets only. Quantity: About five per floret. Filament length: About 2 mm. Filament color: Close to 145C. Anther size: About 0.5 mm by 2 mm. Anther shape: Narrowly oblong. Anther color: Close to 12B. Pollen amount: Scarce. Pollen color: Close to 14A. Gynoecium: Present on both ray and disc florets. Quantity: One per floret. Pistil length: About 5 mm. Style length: About 4.5 mm. Style color: Close to 150C. Stigma diameter: About 1 mm. Stigma shape: Cleft, decurrent. Stigma color: Close to 153D. Ovary color: Close to 157C.

*Seeds and fruits*.—To date, seed and fruit production have not been observed on plants of the new *Chrysanthemum*.

Pathogen & pest resistance: Plants of the new *Chrysanthemum* have been observed to be resistant to Fusarium Wilt (*Fusarium oxysporum* spp. *chrysanthemi* (FoNL1)) and White Rust (*Puccinia horiana* (PhNL1 and PhBE6)). To date, plants of the new *Chrysanthemum* have not been observed to be resistant or tolerant to pests and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFDLIC4' as illustrated and described.

* * * * *